(12) United States Patent
Boedeker et al.

(10) Patent No.: US 7,174,889 B2
(45) Date of Patent: Feb. 13, 2007

(54) DEVICE FOR INSERTION OF ENDOTRACHEAL TUBE

(75) Inventors: Benje Boedeker, Omaha, NE (US); Scott Hofmann, Omaha, NE (US)

(73) Assignee: Board of Regents of the University of Nebraska by and on behalf of the University of Nebraska Medical Center, Omaha, NE (US)

( * ) Notice: Subject to any disclaimer, the term of this patent is extended or adjusted under 35 U.S.C. 154(b) by 0 days.

(21) Appl. No.: 10/859,413

(22) Filed: Jun. 2, 2004

(65) Prior Publication Data

US 2005/0268917 A1    Dec. 8, 2005

(51) Int. Cl.
*A61M 16/00* (2006.01)

(52) U.S. Cl. .............. 128/200.26; 128/207.14

(58) Field of Classification Search ......... 128/207.15, 128/207.14, 200.26, 207.29, 207.16
See application file for complete search history.

(56) References Cited

U.S. PATENT DOCUMENTS

| | | | | |
|---|---|---|---|---|
| 3,707,301 | A | * | 12/1972 | Rauls ...................... 285/9.2 |
| 4,673,398 | A | * | 6/1987 | Turner et al. .............. 604/264 |
| 5,024,220 | A | * | 6/1991 | Holmgreen et al. ... 128/207.18 |
| 5,052,386 | A | | 10/1991 | Fischer, Jr. |
| 5,297,546 | A | * | 3/1994 | Spofford et al. ....... 128/207.14 |
| 5,623,921 | A | | 4/1997 | Kinsinger et al. |
| 5,694,929 | A | | 12/1997 | Christopher |
| 5,873,362 | A | | 2/1999 | Parker |
| 5,937,860 | A | * | 8/1999 | Cook .................... 128/207.15 |
| 5,964,217 | A | | 10/1999 | Christopher |
| 6,079,409 | A | | 6/2000 | Brain |
| 6,257,236 | B1 | | 7/2001 | Dutkiewicz |
| 6,422,239 | B1 | * | 7/2002 | Cook ................... 128/207.15 |
| 6,634,354 | B2 | | 10/2003 | Christopher |
| 6,668,821 | B2 | | 12/2003 | Christopher |
| 6,705,320 | B1 | * | 3/2004 | Anderson ............. 128/207.14 |
| 6,705,321 | B2 | * | 3/2004 | Cook ................... 128/207.15 |
| 6,892,731 | B2 | * | 5/2005 | Cook ................... 128/207.15 |
| 2001/0032646 | A1 | | 10/2001 | Christopher |
| 2001/0050082 | A1 | | 12/2001 | Christopher |
| 2002/0108610 | A1 | | 8/2002 | Chrisopher |

OTHER PUBLICATIONS

Joo, Hwan and Rose, Keith, "Fastrach—a new intubating laryngeal mask airway: successful use in patients with difficult airways", *J. Anaesth.*, 1998, vol. 45, No. 3, pp. 253-256.

Jaeger, J. Michael and Durbin, Jr. Charles G., "Special Purpose Endotracheal Tubes", *Respitory Care*, 1999, vol. 44, No. 6, pp. 661-685.

Goto, H. and McKeag, B., "Continuous Patient Oxygenation During Endotracheal Intubation Through the LMA-Fastrack™", *Anesthesia & Analgesia*, 2001, vol. 93, pp. 766-767.

Arndt, George A., Topp, John, Hannah, Jane, McDowell, Thomas S., Lesko, Anita, "Intubation via the LMA using a Cook retrograde intubation kit", *Equipment Reports, Can J Anaesth*, 1998, vol. 5, No. 3, pp. 257-260.

Pennant, John H. and Joshi, Girish P., Intubation through the Laryngeal Mask Airway, *Anesthesiology*, Oct. 1995, vol. 83, No. 4, pp. 891-892.

* cited by examiner

*Primary Examiner*—Teena Mitchell
(74) *Attorney, Agent, or Firm*—Patterson & Sheridan, L.L.P.

(57) ABSTRACT

The present invention provides an apparatus for advancing an endotracheal tube through and along the length a patient's larynx with a laryngeal mask airway in place and without interrupting ventilation.

12 Claims, 7 Drawing Sheets

DEVICE FOR INSERTION OF ENDOTRACHEAL TUBE

FIELD OF THE INVENTION

This invention relates generally to the field of endotracheal intubation of a patient where a laryngeal mask airway is in place.

BACKGROUND OF THE INVENTION

Endotracheal tubes are often used to ventilate patients with who may be conscious, semi-conscious or unconscious. The conventional approach requires the physician to insert a rigid laryngoscope blade into the patient's mouth and pharynx. Delivery of ventilation and/or oxygen typically is interrupted during this period. The endotracheal tube is then inserted into place while the laryngoscope blade keeps the patient's airway open.

A need exists for an improved device to guide insertion of an endotracheal tube and ensure that the patient's airway is open, and that also allows the patient to continue to receive air/oxygen during the insertion process. Maintaining a patient's airway and assuring ventilation/oxygenation is a critical part of patient care. Conventional intubation by direct laryngoscopy can be difficult and sometimes impossible. Alternative methods may be needed to secure the airway with intubation. Use of the laryngeal mask airway (LMA) has become a popular way of dealing with the difficult airway. It often allows ventilation of the patient if intubation is unsuccessful. Use of the LMA can then assist in the intubation of the trachea and securing the airway. An endotracheal tube can be advanced down the lumen of the LMA and inserted into the trachea. Often this can be accomplished blindly. With present technology, the placement of the endotracheal tube and removal of the LMA are done with the patient not being ventilated. This can lead to oxygen desturation and hypoxia.

Laryngeal masks have been used for many years for several purposes. Sometimes it is necessary to replace a laryngeal mask airway with an endotracheal tube. The present invention provides embodiments of a tubular "push rod" for inserting an endotracheal tube through a laryngeal mask airway as well as methods for using such a push-rod. Because the push rod of the present invention is hollow, the endotracheal tube may be advanced along the length of the patient's larynx without interrupting ventilation.

SUMMARY OF THE INVENTION

Laryngeal mask airways commonly are used for supraglottic airway management; however, sometimes it is necessary to replace such a supraglottic airway with secured endotracheal intubation. Embodiments according to the present invention accomplish this replacement by providing a tubular push rod or stylette to aid in inserting the endotracheal tube into a patient's airway while the laryngeal mask airway is in place without interrupting the flow of air to the patient.

Thus, in one embodiment, the present invention provides a push rod for inserting an endotracheal tube into a patient where the patient has a laryngeal mask airway in place, comprising a tubular body, and a tapered end, wherein the tapered end is adapted to couple with the endotracheal.

In yet another embodiment, the present invention provides a method of intubating a patient with an endotracheal tube where the patient has a laryngeal mask airway in place, comprising inserting a push rod comprising a tubular body, and a tapered end into a proximal end of the endotracheal tube, inserting a distal end of the endotracheal tube into a tubular portion of the laryngeal mask airway; and advancing the distal end of the endotracheal tube to a position within the patient.

These and other objects, advantages and features of the present invention will become apparent to those persons skilled in the art upon reading the details of the structure of the device, formulation of compositions and methods of use, as more fully set forth below.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments that are illustrated in the appended drawings. It is to be noted, however, that the appended drawings illustrate only certain embodiments of this invention and are therefore not to be considered limiting of its scope, for the present invention may admit to other equally effective embodiments.

DETAILED DESCRIPTION

Before the present devices and methods of intubation are described, it is to be understood that this invention is not limited to the particular methodology or apparatus described, as such methods or apparatus may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a factor" refers to one or mixtures of factors, and reference to "the method of production" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. For example, additional description of apparatus or methods for intubation with a laryngeal mask in place described herein include those described in U.S. Pat. Nos. 6,003,514; 5,983,897; 6,240,922; 6,196,224; 6,257,236; 5,694,929; 5,964,217; 6,116,243; 6,021,779; 6,012,452; 6,634,354; 6,668,821; 6,698,430; 6,386,199; 6,261,401; 6,079,409; 6,631,720; 6,626,169; 6,604,525; 6,439,232; and 6,257,236; as well as U.S. published application Nos. 2001/0032646; 2001/0050082; and 2002/0108610.

Laryngeal mask airways commonly used for supraglottic airway management must sometimes be replaced with secured endotracheal airway intubation. The present invention provides a tubular push rod or stylette to aid in inserting an endotracheal tube into a patient's airway while the laryngeal mask airway is in place without interrupting the flow of air to the patient.

Figure 1A:
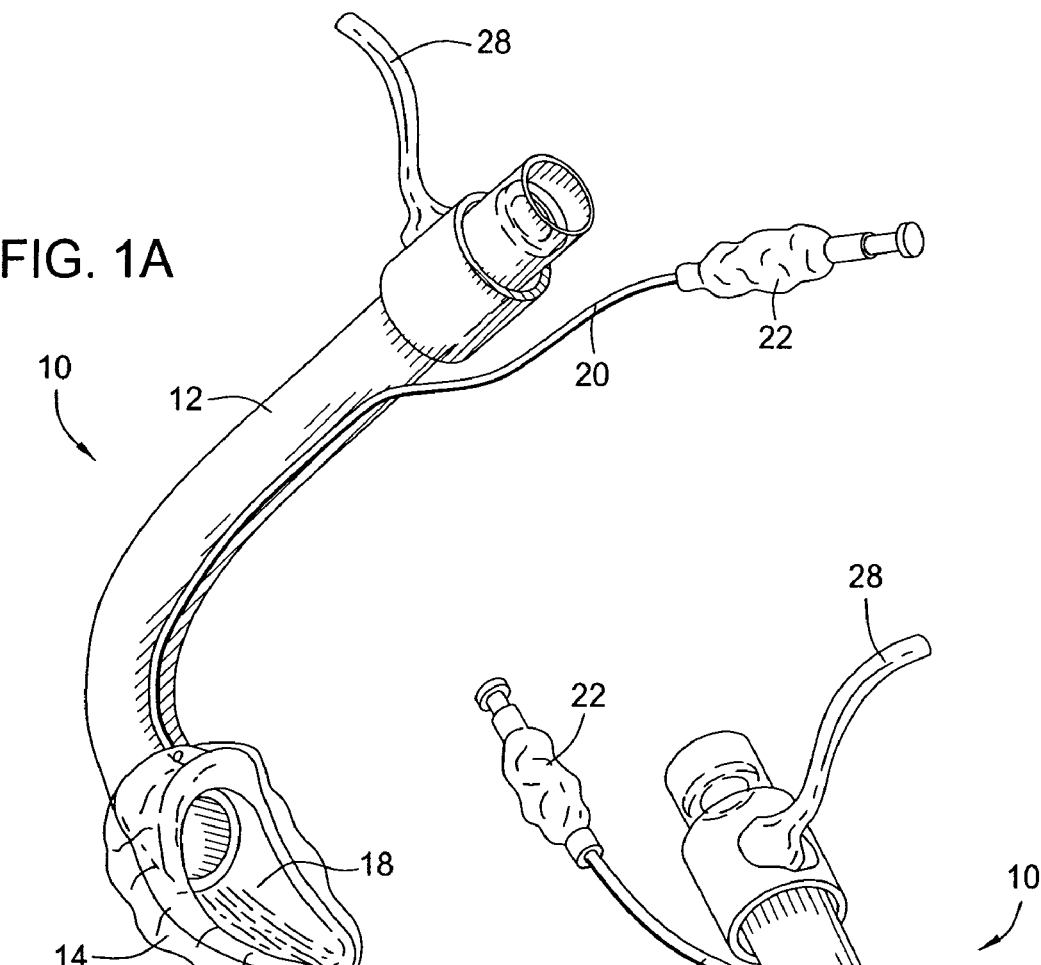
FIG. 1A is a front perspective view of a laryngeal mask airway 10 with a handle 28 for delivery of air/oxygen through guide tube 12.
Figure 1B:
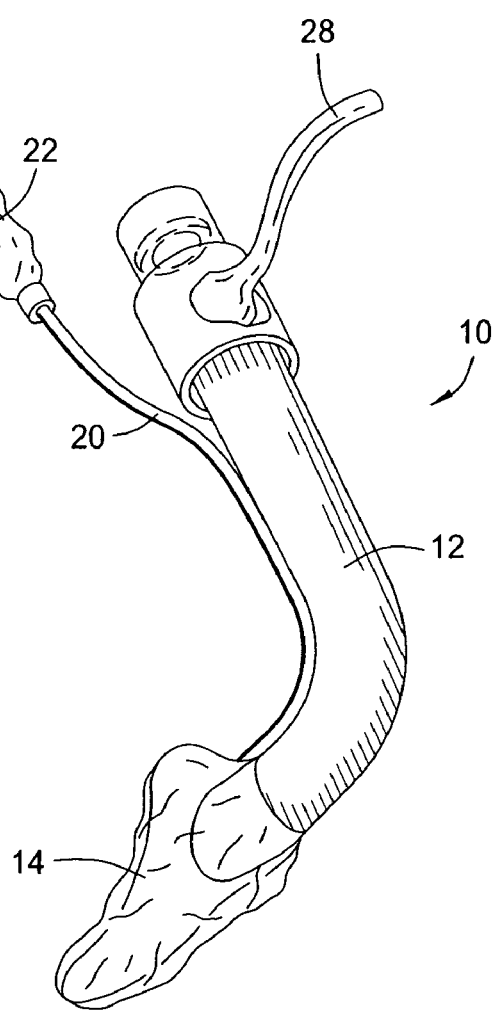
FIG. 1B is a rear perspective view of the laryngeal mask airway corresponding to FIG. 1A.

FIGS. 1A and 1B provide front and rear perspective views of a laryngeal mask airway 10. The embodiment of a laryngeal mask airway shown in these figures includes a tubular guide tube 12 with a laryngeal mask 14 surrounding the distal end of tubular guide tube 12. The size and shape of the guide tube 12 are selected so that the distal portion can be inserted into the patient's mouth and upper airway so that the laryngeal mask 14, once inflated, substantially seals the laryngeal inlet 64 of the patient. The proximal end of the guide tube 12 remains outside of the patient's mouth.

Figure 2:
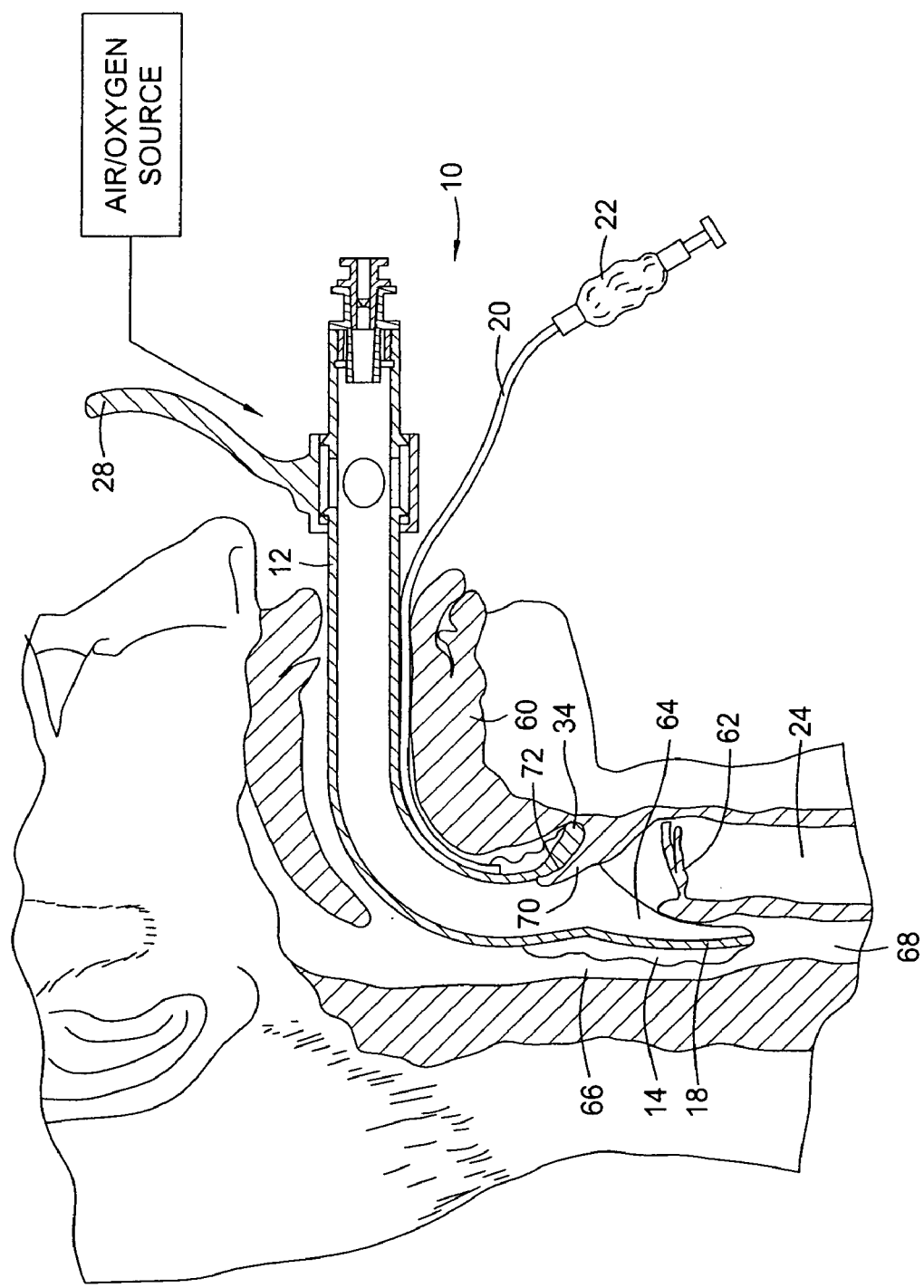
FIG. 2 is a cross-sectional view of a patient's airway after a laryngeal mask airway 10 has been inserted.

Referring to FIG. 2, the guide tube 12 is generally J-shaped to follow the profile of a patient's airway through the mouth, over the tongue 60, and into the laryngopharynx 66 just above the opening to the larynx 62. The guide tube 12 is shaped to prevent the patient's tongue 60 from obstructing access to the trachea 24, while also defining a channel for later insertion of an endotracheal tube. The guide tube 12 is typically made of plastic with sufficient strength and rigidity to keep the patient's teeth apart and prevent the patient from biting down on the endotracheal tube, but with flexibility enough to accommodate a wide range of patient sizes and conditions. The inside diameter of the guide tube 12 should be sufficiently large to allow an endotracheal tube 16 to freely pass through the guide tube 12, as shown for example in FIG. 4A. Handle 28 allows manipulation of the guide tube 12.

The laryngeal mask 14 comprises a central support member 18 extending outward from the guide tube 12 to an inflatable member. The laryngeal mask 14 is preferably made of a soft, flexible material (e.g., a polymer or rubber) to enable it to be advanced into position without injury to the patient and to create a substantially air-tight seal about the laryngeal inlet 64. The degree of inflation of the laryngeal mask 14 can be adjusted through a small inflation tube 20 and air valve 22. Alternatively, the laryngeal mask 14 can be a cushion made of a soft, spongy material that is not inflatable, and can be formed, for example, by injection blow molding, rotational molding, or dip molding. The laryngeal mask 14 and its central support member 18 are shaped to meet several requirements. The lower portion of the laryngeal mask 14 substantially blocks the esophagus 68 to minimize the risk of regurgitation of stomach contents and the passage of air into the stomach. The upper portion of the laryngeal mask 14 guides the distal end of the guide tube 12 into alignment with the laryngeal inlet 64 as the guide is inserted along the patient's airway.

In the embodiment shown in the figures, the laryngeal mask 14 is generally boot-shaped when inflated. The lower portion of the laryngeal mask 14 forms the toe of the boot, which blocks the esophagus 68. The lower portion of the laryngeal mask 14 also helps to align the distal opening of the guide tube 12 with the patient's laryngeal inlet 64. After the laryngeal mask 14 is inflated, the upper portion of the laryngeal mask 14 substantially fills the laryngopharynx 66 at the level of the laryngeal inlet 64. The upper portion of the laryngeal mask 14 surrounds the laryngeal inlet 64 so that the distal opening of the guide tube 12 is sealed against the laryngeal inlet 64. Thus, substantially all of the gas inhaled or exhaled by the patient passes through the guide tube 12. Also seen in FIG. 2 is the epiglottis 70 and the epiglottic vallecula 72.

The upper portion of the mask 14 surrounding the distal opening of the guide tube 12 is optimally canted to complement the natural angle of the laryngeal inlet 64. The distal end of the guide tube 12 also can be beveled at this complementary angle. This enables the laryngeal mask airway 10 to directly engage the laryngeal inlet 64 along the longitudinal axis of the patient's airway as the guide tube 12 is advanced. The shape of the upper portion of the laryngeal mask 14 further helps to guide the distal opening of the guide tube 12 so that it is axially aligned with the laryngeal inlet 64 and abuts the laryngeal inlet 64 in an end-on relationship as the guide is inserted along the patient's airway.

Figure 3A:
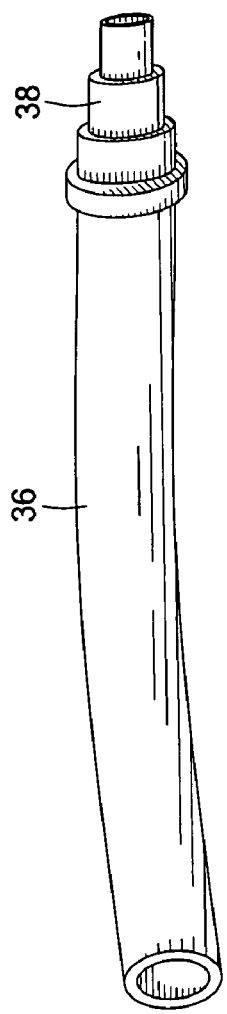
FIG. 3A is a side view perspective of one embodiment of a push rod 36 with a connecting end 38 according to the present invention.
Figure 3B:
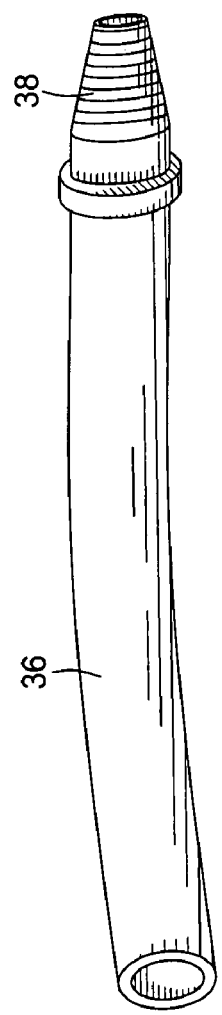
FIG. 3B is a side view perspective of another embodiment of a push rod 36 according to the present invention.
Figure 3C:
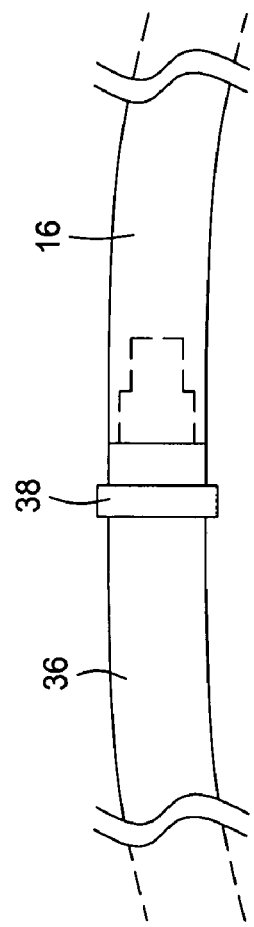
FIG. 3C is a side view perspective of the embodiment of the push rod 36 shown in FIG. 3A connected to an endotracheal tube 16.

FIGS. 3A through 3D provide side view perspectives of embodiments of the tubular push rods or stylettes according to the present invention. FIG. 3A shows an embodiment where the push rod 36 has a graduated or tapered "alligator-type" end 38 that is adapted to couple with endotracheal tubing. The embodiment of push rod 36 in FIG. 3B also has a graduated or tapered end 38; however in this embodiment the graduation is not stepped, but is tapered smoothly. The push rod 36 in many embodiments will range from about 2.0 mm to about 9.0 mm in diameter, and preferably will be about 4.0 mm in diameter to about 6.0 in diameter. The graduated or tapered configuration of the end 38 allows for the push rod 36 to be coupled to a variety of sizes of endotracheal tubing 16, as shown in one embodiment in FIG. 3C. For example, the graduated or tapered end 38 may, at larger end 38b, range from about 2.0 mm to about 9.0 mm in diameter, and preferably will be about 4.0 mm in diameter to about 6.0 mm in diameter. At the smaller end 38c of tapered end 38, the diameter will range from about 1.0 mm to about 8.0 mm in diameter, and preferably will be in the about 2.0 mm to about 5.0 mm diameter range to accommodate the endotracheal tubing.

The push rod 36 may comprise any biocompatible material, preferably medical grade biocompatible material, such as various plastics, polymers, metals, and the like. In some embodiments, push rod 36 is semi-flexible; however, in other embodiments, push rod 36 is substantially rigid. In embodiments where push rod 36 comprises a plastic or polymer material, tapered end 38 may be formed by heat molding. Alternatively, other modes of manufacture may be employed for push rod 36, such as blow molding, rotational molding, dip molding, or machining. In one embodiment, the push rod 36 comprises semi-rigid medical grade polyvinyl chloride.

Figure 3D:
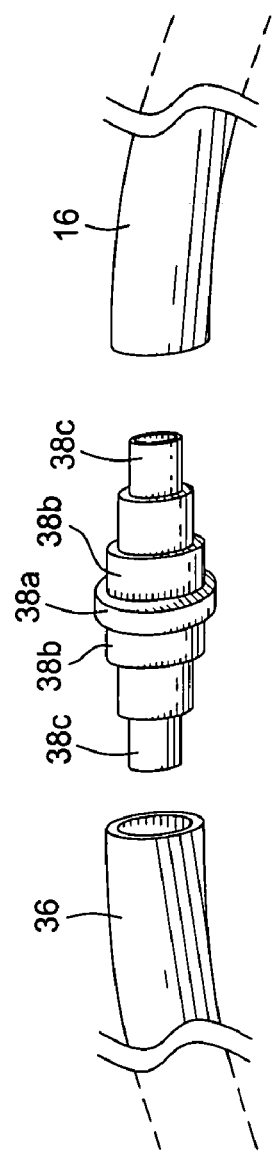
FIG. 3D is another embodiment of a push rod 16 according to the present invention, where an alligator-type connecting end 38a of the push rod 16 is actually a separate component.

FIG. 3D shows an alternative embodiment of push rod 36, where the tapered end 38 is a separate component. In the embodiment shown, tapered end 38a is tapered bidirectionally, with the larger diameter portion at 38b, and two smaller diameter portions at 38c.

The present invention also provides methods for using the push rods or stylettes according to the present invention. Generally, the curved distal portion of the guide tube 12 is first inserted into the patient's mouth and laryngopharynx 66 with the laryngeal mask 14 deflated, as shown in FIG. 2. FIG. 2 shows a laryngeal mask airway 10 inserted into a patient's airway, showing positioning of the airway in relation to the larynx 62, esophagus 68, epiglottis 70 and epiglottic vallecula 72. The lower portions of the central support member 18 and laryngeal mask 14 extend into the esophagus 68. The upper portions of the central support member 18 and the laryngeal mask 14 surround the laryngeal inlet 64. A protrusion 34 on the anterior portion of the distal tip of the guide tube 12 or central support member 18 is inserted to the patient's epiglottic vallecula 72 (the notch between the base of the tongue 60 and the epiglottis 70). The protrusion 34 pushes on the epiglottic vallecula 72, which tends to lift the epiglottis 72 from the laryngeal inlet 64 and helps to ensure patency of the patient's airway.

After the distal portion of the guide tube 12 and the laryngeal mask 14 are appropriately positioned relative to the laryngeal inlet 64, the laryngeal mask 14 is inflated via the inflation tube 20 to establish a seal around the laryngeal inlet 64. The lower portion of the inflated laryngeal mask 14 substantially blocks the esophagus 68. The upper portion of the inflated laryngeal mask 14 substantially fills the laryngopharynx 66 adjacent to the laryngeal inlet 64, thereby sealing the distal opening of the guide tube 12 in fluid communication with the laryngeal inlet. The side portions of the inflated laryngeal airway mask 14 squeeze the sides of the epiglottis 70, which also tends to lift the epiglottis 70 from the laryngeal inlet 64.

Figure 4A:
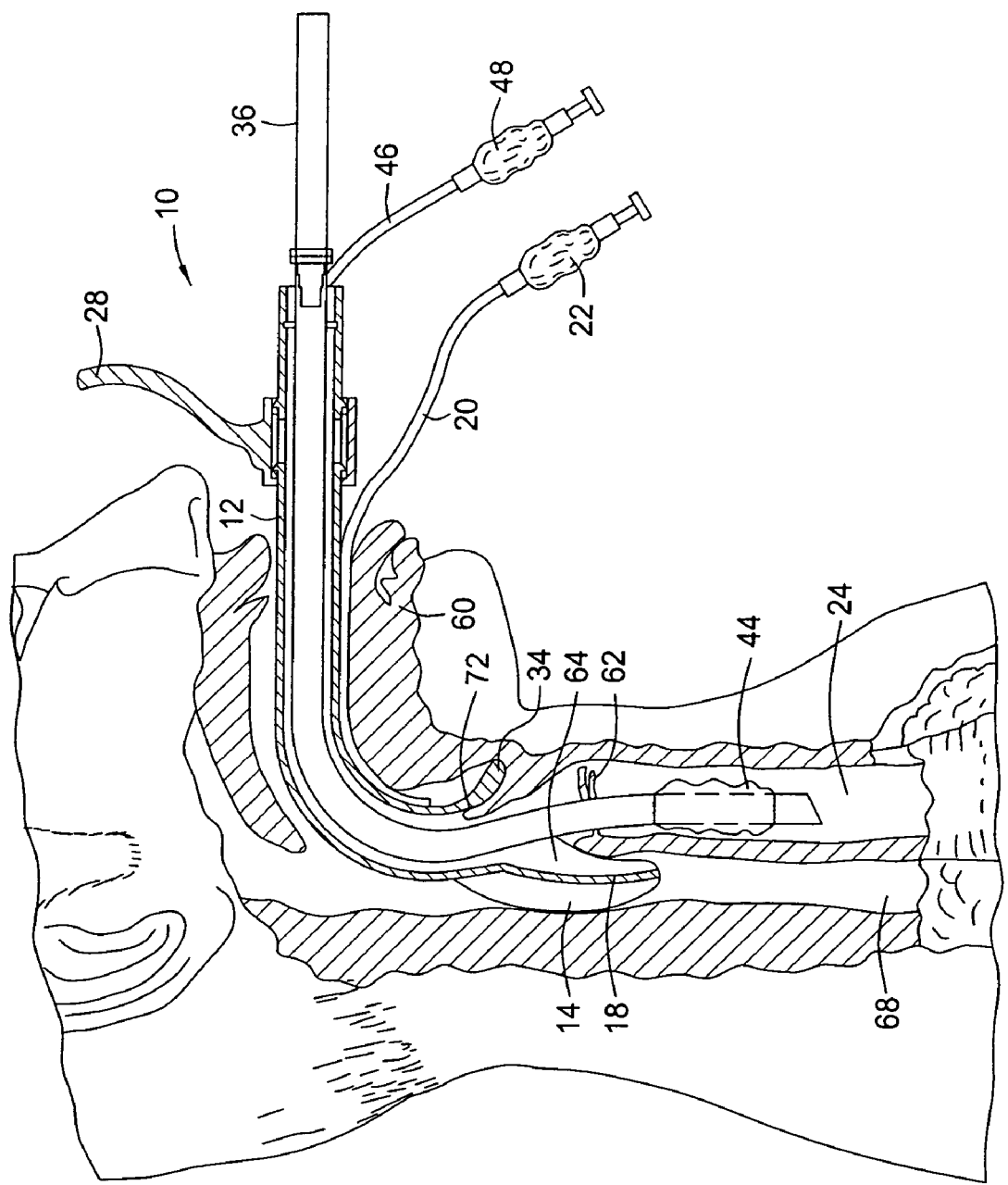
FIG. 4A is a cross-sectional view of the laryngeal mask airway 10 and the patient's airway after an endotracheal tube 16 has been inserted through the laryngeal mask airway 10.

After the patient's condition has been stabilized to some degree during initial resuscitation, an endotracheal tube 16 may be inserted. An endotracheal tube 16 attached at its proximal end (the end outside the patient) to push rod 36 is advanced into and through guide tube 12. With the present invention, resuscitation, oxygenation, and/or artificial ventilation continue without interruption while the endotracheal tube 16 is advanced along the guide tube 12 and through the laryngeal mask 14 to a position within the trachea past the larynx 62. FIG. 4A is a cross-sectional view of the laryngeal mask airway 10 during insertion of the endotracheal tube 16.

In the preferred embodiment, the push rod 36 is an annular, flexible plastic tube, as shown in various embodiments in FIGS. 3A through 3D, with a graduated or tapered end 38 to engage with the endotracheal tube 16. The graduated or tapered end 38 of the push rod 36 preferably provides a snug, frictional fit between the exterior of the tapered end 38 and the interior of the endotracheal tube 16 so that the push rod 36 may advance the endotracheal tube smoothly and reliably through guide tube 12. The shape of the guide tube 12, the central support member 18, and laryngeal mask 14 tend to align the distal opening of the guide tube 12 with the larynx 62 so that the endotracheal tube 16 will pass through the opening between the vocal cords.

Figure 4B:
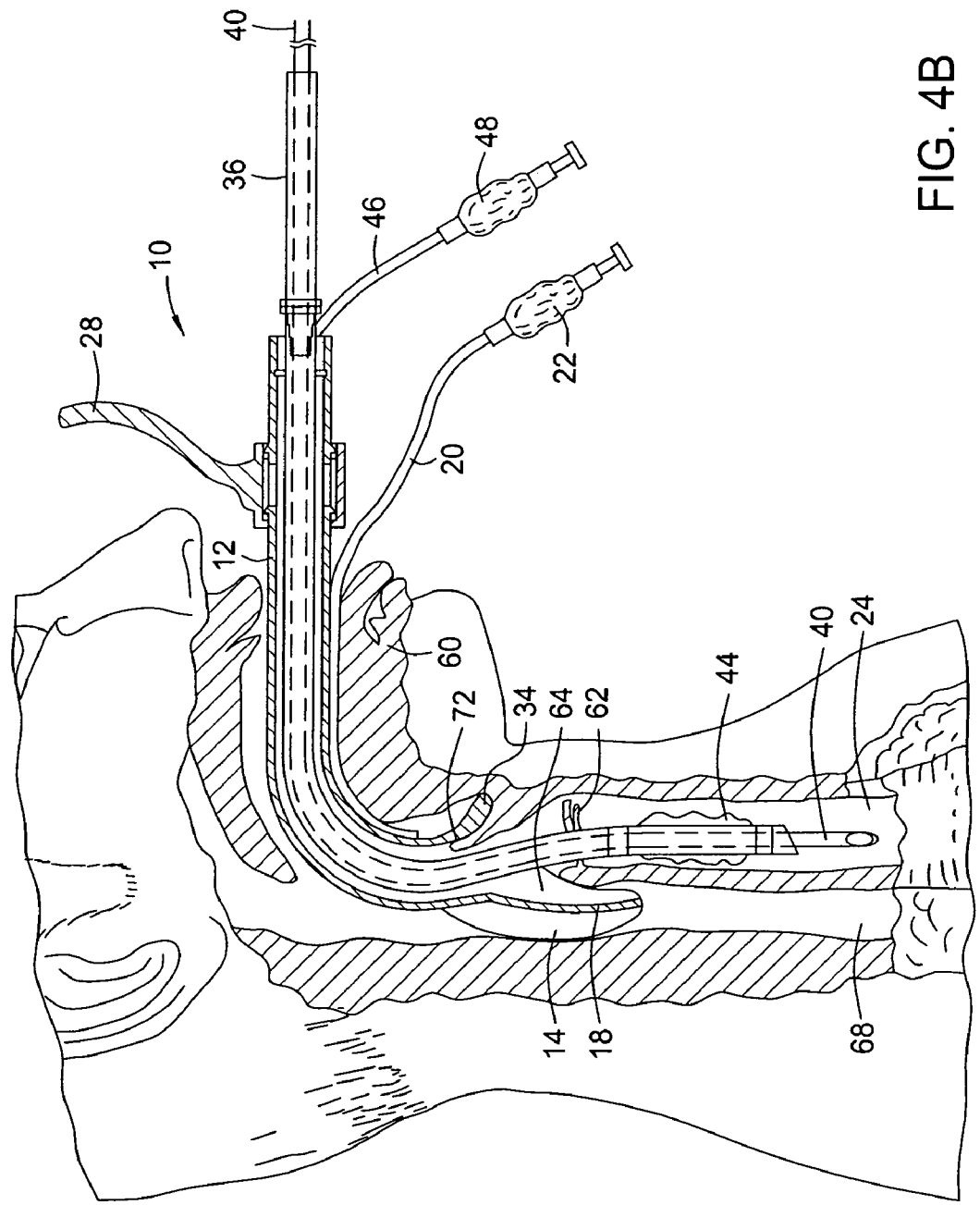
FIG. 4B is a cross-sectional view of the laryngeal mask airway 10 and the patient's airway after an endotracheal tube 16 and an endoscope probe 40 has been inserted through the laryngeal mask airway 10.

FIG. 4B shows an embodiment of the present invention where an endoscope probe 40 is used to assist in positioning push rod 36. In this embodiment, the endoscope probe 40 is inserted inside the push rod 36, and the entire endoscope/push rod combination is advanced into guide tube 12. After emerging from the distal end of the guide tube 12, the direction of the distal tip of the endoscope probe 40 can be controlled by the physician. This allows the physician to carefully guide the endoscope probe 40 and endotracheal tube 16 to a position past the larynx 62 while resuscitation continues. In such a case, the outside diameter of the endotracheal tube 16 is small enough to allow free passage of air between the inside diameter of the guide tube 12, and the outside diameter of the endotracheal tube 16. Many conventional endoscopes include a suction channel that extends the length of the fiber optic probe to the distal tip. This feature can be used to suction mucus or other secretions from the patient's airway as the endoscope/endotracheal tube assembly is inserted. An endoscope 40 may not be needed at all due to the anatomical alignment provided by the laryngeal mask 14, which permits "blind" intubation of the patient. In any event, because of the tubular configuration of the push rod 36, the patient is being ventilated throughout the intubation process so the normal risks associated with intubation are not as serious if delays are encountered during the intubation process.

Figure 5:
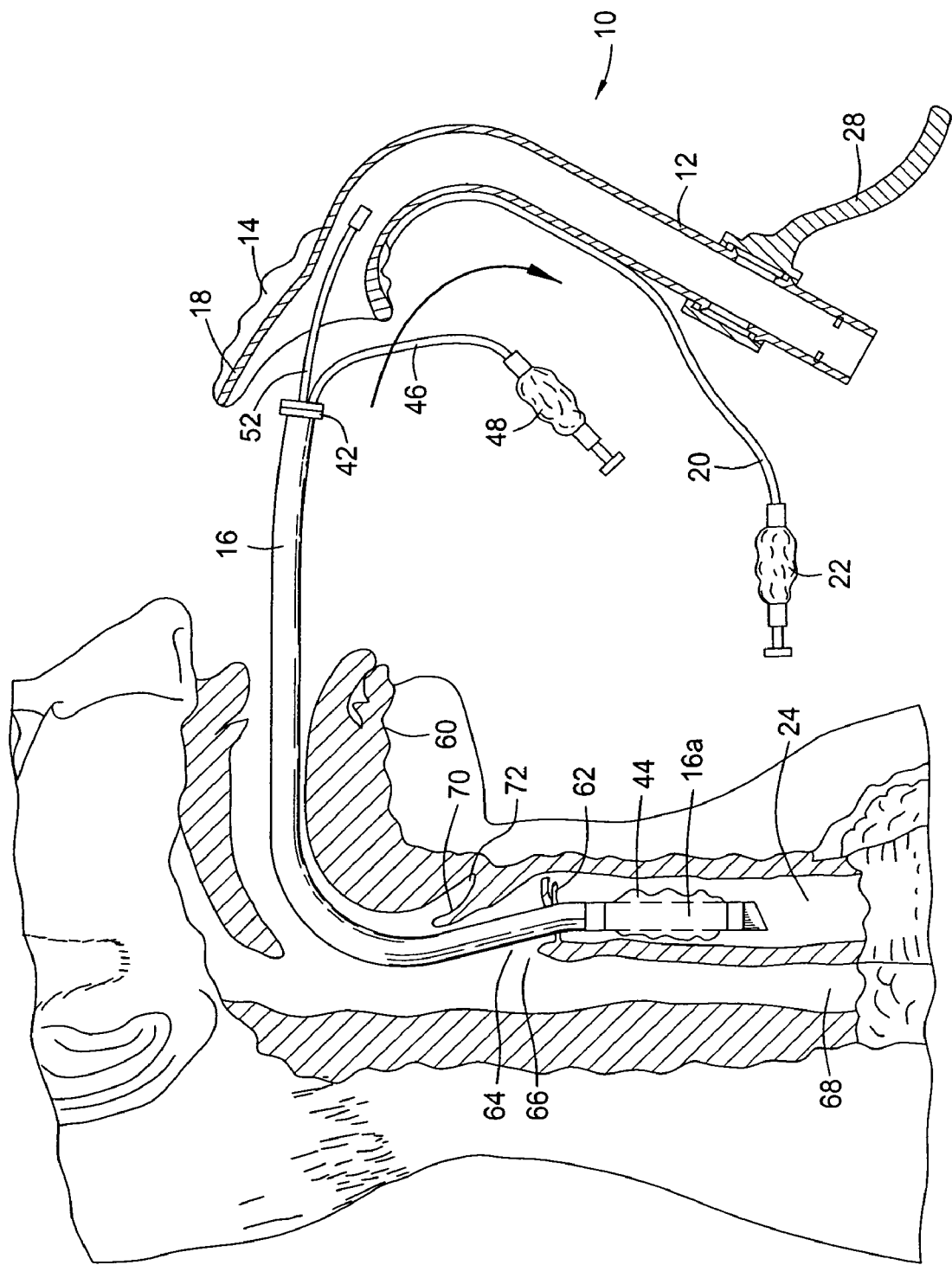
FIG. 5 is a cross-sectional view of the laryngeal mask airway 10 and the patient's airway after the laryngeal mask 14 has been deflated and the laryngeal mask airway 10 has been removed, leaving the endotracheal tube 16 in place in the patient's airway.

Once the endotracheal tube 16 is positioned within the airway, the laryngeal mask 14 is deflated and the guide tube 12 is removed optionally using, e.g., a handle 28, while leaving the endotracheal tube 16 in place within the trachea, as illustrated in FIG. 5. Alternatively, the guide tube 12 can be left in place to serve as an oral airway and to protect the endotracheal tube 16 from being bitten by the patient's teeth. However, the laryngeal mask 14 should be deflated if the device is to be left in place in the patient's airway for an extended period of time to minimize damage to the mucous lining. FIG. 5 shows an embodiment where the push rod 36 has been removed from the end of the endotracheal tube 16, and a fitting or cap 42 that can accommodate attachment to tubing 52 and a ventilator is inserted.

Figure 6:
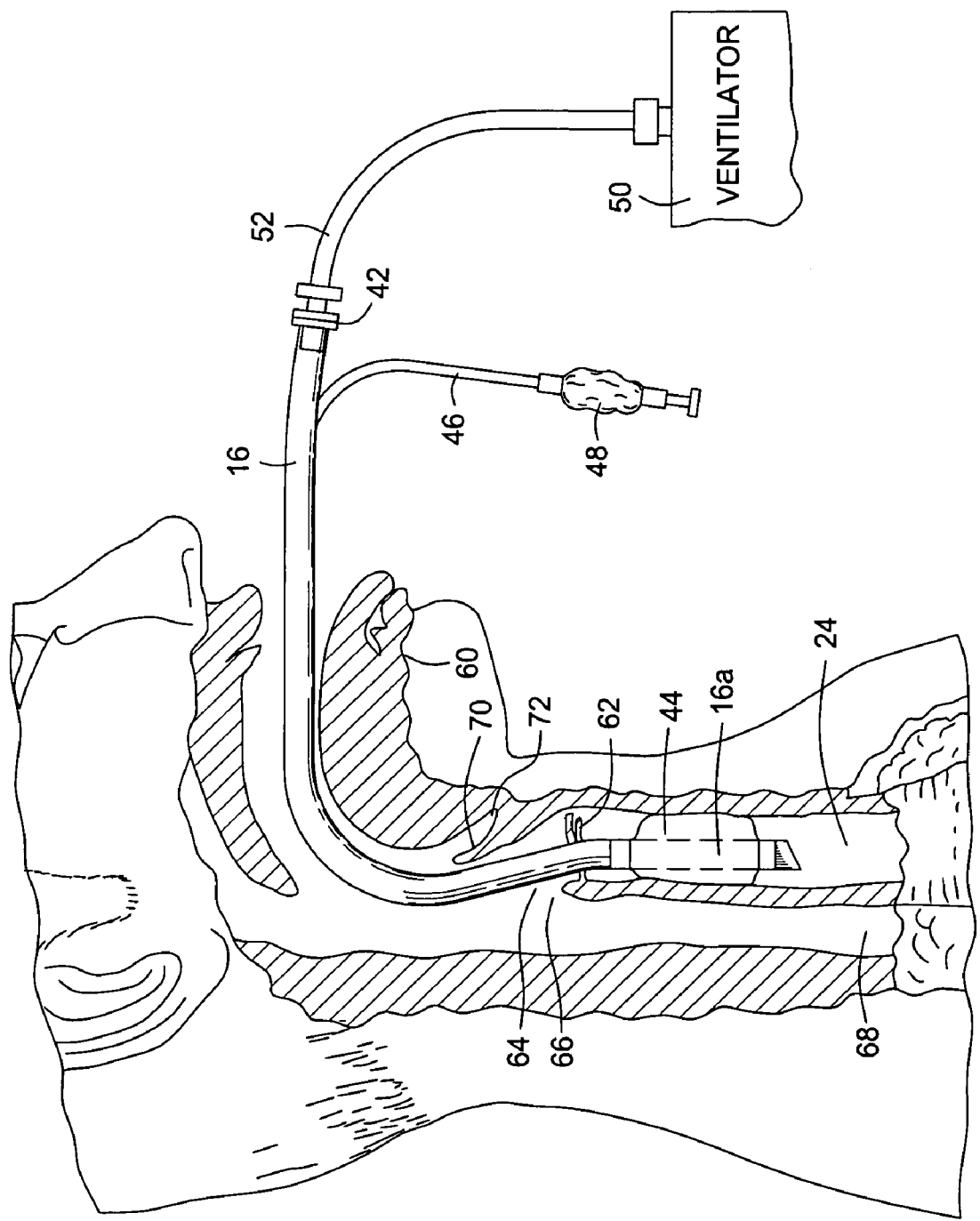
FIG. 6 is a cross-sectional view of the patient's airway after the cuff 44 of the endotracheal tube 16 has been inflated and the patient has been connected to a ventilator 50.

Once the laryngeal mask airway 10 is removed, a cuff 44 on the endotracheal tube 16 is then inflated via an inflation tube 46 and air valve 48 to establish a seal for the airway provided by the endotracheal tube 16 (shown in phantom at 16a through cuff 44). Finally, a ventilator 50 is connected to the proximal end of the endotracheal tube 16 to ventilate the patient, as shown in FIG. 6. Alternatively, the patient can be manually ventilated by connecting a resuscitation bag to the proximal end of the endotracheal tube 16.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, or process to the objective, spirit and scope of the present invention. All such modifications are intended to be within the scope of the invention.

We claim:

1. A system, comprising:
   an endotracheal tube; and
   a push rod for inserting the endotracheal tube into a patient where the patient has a laryngeal mask airway in place, wherein the push rod comprises two separate components comprising:
   a tubular body portion for pushing the endotracheal tube into the patient through the laryngeal mask airway with uninterrupted ventilation, and
   a tapered end portion, wherein the tapered end portion is stepped to a smaller outer diameter towards the endotracheal tube for direct connection to the endotracheal tube.

2. The system of claim 1, wherein a larger end of the tapered end portion ranges from about 2.0 mm to about 9.0 mm in diameter.

3. The system of claim 2, wherein the larger end of the tapered end portion ranges from about 4.0 mm to about 6.0 mm in diameter.

4. The system of claim 1, wherein a smaller end of the tapered end portion ranges from about 1.0 mm to about 8.0 mm in diameter.

5. The system of claim 4, wherein the smaller end of the tapered end portion ranges from about 2.0 mm to about 5.0 mm in diameter.

6. The system of claim 1, wherein the push rod comprises a biocompatible material.

7. The system of claim 6, wherein the biocompatible material is medical grade material.

8. The system of claim 6, wherein the biocompatible material is a plastic, a polymer or metal.

9. The system of claim 6, wherein the biocompatible material is medical grade polyvinyl chloride.

10. The system of claim 1, wherein the push rod is semi-flexible.

11. The system of claim 1, wherein the push rod is substantially rigid.

12. The system of claim 1, wherein the tapered end portion is bidirectionally tapered.

* * * * *